United States Patent [19]

Lee et al.

[11] 4,348,516
[45] Sep. 7, 1982

[54] MICROBIOLOGICAL METHYLATION OF AMINOGLYCOSYL-AMINOGLYCOSIDES

[75] Inventors: Bong K. Lee; Gerald H. Wagman, both of East Brunswick; Dinanath F. Rane, Emerson; Joseph A. Marquez, Montclair; Peter J. L. Daniels, Cedar Grove, all of N.J.

[73] Assignee: Schering Corporation, Kenilworth, N.J.

[21] Appl. No.: 158,850

[22] Filed: Jun. 12, 1980

Related U.S. Application Data

[62] Division of Ser. No. 51,790, Jun. 25, 1979, Pat. No. 4,234,685.

[51] Int. Cl.$^3$ .................... A61K 31/71; C07H 15/22
[52] U.S. Cl. .................... 536/10; 424/180; 435/80; 536/17 R
[58] Field of Search .................... 536/10, 17 R

[56] References Cited

U.S. PATENT DOCUMENTS 4,044,123  8/1977  Daniels et al. .................... 536/10
4,051,315  9/1977  Godfrey et al. .................... 536/10
4,066,752  1/1978  Mallams et al. .................... 536/10

Primary Examiner—Johnnie R. Brown
Attorney, Agent, or Firm—Gerald S. Rosen; Bruce M. Eisen; Carver C. Joyner

[57] ABSTRACT

The microorganisms *Micromonospora inyoensis* 1550F-1G and *M. purpurea* strain 1124 each microbiologically convert tobramycin, kanamycin A, kanamycin B and dibekacin to their respective 3''-N-methyl and 3''-N-methyl-4''-C-methyl derivatives. The derivatives exhibit significant activity against representative gram positive and gram negative bacteria and may also be converted to other derivatives which have significant antibacterial activity.

8 Claims, No Drawings

MICROBIOLOGICAL METHYLATION OF AMINOGLYCOSYL-AMINOGLYCOSIDES

This is a division of application Ser. No. 051,790, filed June 25, 1979, now U.S. Pat. No. 4,234,685.

FIELD OF THE INVENTION

This invention relates to a microbiological transformation of tobramycin, kanamycin A, kanamycin B and dibekacin. More particularly, this invention relates to a microbiological process for methylating tobramycin, kanamycin A, kanamycin B and dibekacin by the use of either *Micromonospora purpurea* strain 1124 or *Micromonospora inyoensis* 1550F-1G, to the products obtained thereby, to certain chemical derivatives thereof, and to the use of such compounds as antibacterial agents. In particular, this invention relates to 3''-N-methyl tobramycin, 3''-N-methyl-4''-C-methyl tobramycin, 3''-N-methyl kanamycin A, 3''-N-methyl-4''-C-methyl kanamycin A, 3''-N-methyl kanamycin B, 3''-N-methyl-4''-C-methyl kanamycin B, 3''-N-methyl dibekacin, 3''-N-methyl-4''-C-methyl dibekacin, the 5-epi, 5-deoxy, 5-epiamino-5-deoxy, 5-epiazido-5-deoxy, 5-epifluoro-5-deoxy analogs of the foregoing, and the 1-N-X derivatives of all of the foregoing, wherein X is an alkyl or acyl function of up to 8 carbon atoms which may be optionally substituted by one or more amino, alkylamino, or hydroxy functions, with the proviso that when more than one optional function is involved such functions cannot be on the same carbon atoms, and to the non-toxic pharmaceutically acceptable acid addition salts thereof.

DESCRIPTION OF THE PRIOR ART

Tobramycin (nebramycin factor 6) is a microbiological elaborate of *Streptomyces tenebrarius* ATCC 17920 or ATCC 17921, and is a member of complex comprising several antibiotics. The fermentation conditions are described in Antimicrobial Agents and Chemotherapy 1967, pp. 314–318 and the structure of tobramycin and proof therefor is set forth in the same journal 1970, pp. 309–313. Nebramycin complex is also described in the U.S. Pat. No. 3,691,279.

Kanamycins A and B are well known antibiotics whose physical properties are described in the *Index of Antibiotics From Actinomycetes*, University of Tokyo Press (1967), page 30, and dibekacin, another well-known antibiotic, is the 3',4'-dideoxy analog of Kanamycin B. The structural formulae of all such compounds are well known.

DESCRIPTION OF THE INVENTION

*Micromonospora inyoensis* 1550F-1G (on public deposit with an accession number of NRRL 5742) or *Micromonospora purpurea* strain 1124 (on public deposit with an accession number of NRRL 8102), when fermented in an aqueous nutrient medium containing an assimilable source of methionine under aerobic conditions, do not produce a measurable amount of any substance having antibacterial activity. However, when cultivated under substantially identical conditions in the presence of tobramycin, kanamycin A, kanamycin B or dibekacin new substances having substantial antibacterial activity are produced. Chromatographic investigations of the substances reveal the presence of a complex of at least two discreet entities which, on the basis of physicochemical investigation, have been found to be 3''-N-methyl tobramycin and 3''-N-methyl-4''-C-methyl tobramycin when tobramycin is added to the fermentation. In like manner, when kanamycin A is added to the fermentation, 3''-N-methyl kanamycin A and 3''-N-methyl-4''-C-methyl kanamycin A are produced. When kanamycin B is added to the fermentation, 3''-N-methyl kanamycin B and 3''-N-methyl-4''-C-methyl kanamycin B are produced and when dibekacin is added to the fermentation the 3''-N-methyl dibekacin and 3''-N-methyl-4''-C-methyl dibekacin are produced.

Thus, in one of its process aspects, this invention may be described as residing in a process wherein a composition of matter selected from the group consisting of tobramycin, kanamycin A, kanamycin B and dibekacin, is subjected to the methylating action of *Micromonospora inyoensis* 1550F-1G or *Micromonospora purpurea* strain 1124 in an aqueous nutrient medium containing an assimilable source of methionine, under aerobic conditions until methylation is substantially complete to produce the respective 3''-N-methyl and 3''-N-methyl-4''-C-methyl derivatives.

In its product aspect, this invention is described as (a) the 3''-N-methyl-4''-C-methyl derivatives of tobramycin, kanamycin A, kanamycin B and dibekacin, (b) the 5-epi, the 5-deoxy, the 5-epiamino-5-deoxy, the 5-epiazido-5-deoxy, and the 5-epifluoro-5-deoxy analogs of 3''-N-methyl-tobramycin, 3''-N-methyl-4''-C-methyl tobramycin, 3''-N-methyl kanamycin A, 3''-N-methyl-4''-C-methyl kanamycin A, 3''-N-methyl kanamyci B, 3''-N-methyl-4''-C-methyl kanamycin B, 3''-N-methyl dibekacin, and 3''-N-methyl-4''-C-methyl dibekacin and (c) the 1-N-X analogs of (a) and (b) wherein X is an alkyl or acyl moiety having up to 8 carbon atoms optionally substituted by one or more amino, lower alkylamino or hydroxy functions, with the proviso that not more than one optional function can be on the same carbon atom, and to the non-toxic pharmaceutically acceptable salts thereof.

The preferred 1-N-X analogs are those wherein X is alkyl, especially ethyl, propyl and butyl, and when X is aminohydroxylacyl, especially 2-hydroxy-3-aminopropionyl and 2-hydroxy-4-aminobutyryl. The term "lower alkylamino" embraces those functions having up to 8 carbon atoms.

As previously stated, the methylation takes place in a medium contaning an assimilable source of methionine, however, it is not necessary for the nutrient medium to contain methionine as a separate and discreet entity. Methionine may be a constituent of a particular assimilable nutrient medium utilized in the fermentation medium (e.g., soybean meal) or it may be a constituent of several assimilable nutrient materials utilized in the fermentation medium.

The process of this invention is usually initiated by the preparation of a vegetative inoculum, which is utilized in the fermentation process. The inoculum can be prepared with frozen cells and may be effected in any medium in which the microorganisms exhibit good growth. An aqueous nutrient medium containing specific quantities of yeast extract, fish solubles, corn steep, liquor, potato starch, a suitable buffer (e.g., CaCO$_3$) has been found to be an excellent growth medium for *M. inyoensis* 1550F-1G or *M. purpurea* strain 1124. For large scale fermentations (e.g., 50 liters or above), a three step process is advisable, a second germination (inoculum preparation) step being employed. Inocululm preparation is usually effected at a temperature in the range of from about 27° C. to about 37° C., preferably about 30° C. When a second inoculum preparation is employed, it is preferably effected within the same temperature range as the first. In either case, the germination process is conducted under aerobic conditions with agitation.

The fermentation may be effected in substantially the same nutrients as those used for the inoculum preparation. Alternatively, other assimilable sources of carbon and nitrogen may be utilized with the proviso that methionine or assimilable nutrients containing methionine are present. In general, it is not preferred to add the antibiotics (e.g., tobramycin, kanamycin A, kanamycin B or dibekacin) at the commencement of the fermentation but, rather, at from about 24 to about 48 hours after the microorganism has been added to the fermentation medium. The fermentation and isolation processes are effected in substantially the same manner when either the M. inyoensis 1550F-1G or the M. purpurea strain 1124 is utilized.

The fermentation, like the inoculum preparation is conducted at a pH range of from about 6.0 to about 8.0, preferably about 6.8 to about 7.4. The temperature is maintained in the range of from about 24° C. to about 40° C., preferably from about 28° C. to about 35° C. Aeration is employed in fermentations which are conducted in stationary vessels. The process may be monitored after about 24 hours from the addition of the tobramycin, kanamycin A, kanamycin B or dibekacin by chromatographing the products produced by the fermentation. Chromatography is preferably effected on cellulose thin layer plates or on paper and plated against Staphylococcus aureus ATCC 6539P. The preferred solvent system utilized for chromatography depends upon the substrate used in the fermentation. When kanamycin A is the substrate, the solvent system used is chloroform:methanol:concentrated ammonium hydroxide in the ratio by volume of 1:3:1. When kanamycin B, tobramycin or dibekacin are the substrates, the solvent system is chloroform-methanol:17% ammonium hydroxide in the volume ratio of 2:2:1.

Some of the measured $R_f$ values of the methylated compounds produced by the instant process are:

|  | $R_f$ |
| --- | --- |
| Kanamycin A | 0.44 |
| 3"-N—methyl kanamycin A | 0.42 |
| 3"-N—methyl-4"-C—methyl kanamycin B | 0.65 |
| Kanamycin B | 0.15 |
| 3"-N—methyl kanamycin B | 0.33 |
| 3"-N—methyl-4"-C—methyl kanamycin B | 0.47 |
| Tobramycin | 0.52 |
| 3"-N—methyl tobramycin | 0.63 |
| 3"-N—methyl-4"-C—methyl tobramycin | 0.72 |

THE MICROORGANISMS

A culture of Micromonospora inyoensis 1550F-1G is on deposit with the U.S. Department of Agriculture, Northern Utilization Research and Development Division, Peoria, Ill., where it was assigned the accession number NRRL 5742, and is available from the agency upon request. The microorganism is described in U.S. Pat. No. 4,011,390, which issued Mar. 7, 1977, and is entitled "Semi-Synthetic Aminoglycoside Antibiotics and Methods for the Preparation Thereof". The patent describes a process whereby M. inyoensis 1550F-1G incorporates a variety of aminocyclitols and prepares a number of antibiotics which are analogs of sisomicin. The disclosed taxonomical, biochemical and morphological properties in the patent are hereby incorporated by reference.

Another prior art publication wherein M. inyoensis 1550F-1G is described is in The Journal of Antibiotics (Japan) Vol. 28, No. 8, August 1975 (pp. 573–579). The article is entitled "Biotransformation, A New Approach to Aminoglycoside Biosynthesis 1. Sisomicin". The article discloses a number of pseudodisaccharides and pseudotrisaccharides which the microorganism is capable of converting to sisomicin and an even larger number of such compounds which the microorganism appears to be unable to transform. The authors also propose a biosynthetic pathway for the conversion of 2-deoxystreptamine to sisomicin.

Micromonospora purpurea strain 1124, like M. inyoensis 1550F-1G, has the ability to mono-methylate and di-methylate certain aminoglycoside-aminocyclitol antibiotics. The strain is on deposit with the U.S. Department of Agriculture, Northern Utilization Research and Development Division, Peoria, Ill., where it was assigned the accession number NRRL 8102. The microorganism is described as follows:

MICROSCOPIC

The organism exhibits long, branched mycelia, 0.5 microns in diameter. Smooth-walled, spore-like structures are formed terminally, sporophores are not observed.

CHEMICAL

Analysis of whole cells indicates the presence of mesodiaminopimelic acid, xylose and arabinose. The presence of these compounds are indicative of organisms belonging to the genus Micromonospora.

TABLE I
MICROMONOSPORA PURPUREA STRAIN 1124
Growth and Morphology on Various Media

| Medium | | Strain 1124 |
| --- | --- | --- |
| BENNETT'S | (1) | |
| Agar | G | good |
| | S | plicate |
| | C | g5ne, tile red; 55, strong brown |
| | DFP | faint purple |
| | AM | none |
| Czapek- | G | good |
| Sucrose | S | raised, folded |
| Agar | C | g4nc, russet orange; 51, deep orange |
| | DFP | none |
| | AM | none |
| Glucose- | G | poor |
| Asparagine | S | flat |
| Agar | C | g4lc, dusty orange; 53, moderate orange |
| | DFP | none |
| | AM | none |
| Nutrient | G | poor to fair |
| Agar | S | flat to slightly folded |
| | C | g4nc, russet orange; 51, deep orange |
| | DFP | none |
| | AM | none |
| Peptone- | G | poor to fair |
| Glucose | S | slightly raised, plicate |
| Agar | C | g4ne, luggage tan; 55, strong brown |
| | DFP | none |
| | AM | none |
| Potato | G | fair to good |
| Dextrose | S | raised, wrinkled |
| Agar | C | g7ni, rose brown, 20 dark grayish red |
| | FP | faint purple |
| | AM | none |
| Emerson's | G | poor to fair |
| Agar | S | slightly raised, plicate |
| | C | g5lc, copper; 54, brownish orange |

TABLE I-continued
*MICROMONOSPORA PURPUREA STRAIN 1124*
Growth and Morphology on Various Media

| Medium | | Strain 1124 |
|---|---|---|
| | FP | faint yellow |
| | AM | none |
| NZ Amine | G | good |
| Agar | S | raised, furrowed |
| | C | g5ne, tile red; 55, strong brown |
| | DFP | none |
| | AM | none |
| Yeast | G | good |
| Extract | S | raised, folded |
| Glucose | C | g7 ½pL, deep maroon, 47 dark grayish red |
| Agar | DFP | none |
| | AM | none |
| Tomato | G | good |
| Pasts Oat- | S | raised, deeply folded |
| meal Agar | C | g5nc, burnt orange, 35 strong red-orange |
| | DFP | none |
| | AM | none |
| Oatmeal | G | poor to fair |
| Agar | S | flat, granular |
| (ISP #3) | C | g61g, dark redwood: 46 grayish-red brown |
| | DFP | light purple |
| | AM | none |
| Malt Yeast | G | good |
| Extract | S | raised, plicate |
| Agar | C | g51c, copper; 54, brownish orange |
| (ISP #2) | DFP | faint pink |
| | AM | none |
| Inorganic | G | poor |
| Salts | S | |
| Starch | C | |
| Agar | DFP | |
| (ISP #4) | AM | |
| Glycerol | G | poor |
| Asparagine | S | |
| Agar | C | |
| (ISP #5) | DFP | |
| | AM | |
| Water | G | poor |
| Agar | S | |
| | C | |
| | DFP | |
| | AM | |
| Calcium | G | poor |
| Malate | S | |
| Agar | C | |
| | DFP | |
| | AM | |
| Calcium | G | poor |
| Citrate | S | |
| Agar | C | |
| | DFP | |
| | AM | |

TABLE II
Growth, Morphology and Reactions on Various Media
*Micromonospora purpurea* strain 1124

| Medium | | Strain |
|---|---|---|
| Gelatin | G | fair |
| Agar | S | plicate |
| (McDade) | C | g4nc, rose beige; 57, light brown |
| | DFP | none |
| | AM | none |
| | R | hydrolysis of gelatin; positive |
| Starch- | G | fair |
| Beef Agar | S | plicate |
| | C | g5ia, bright peach; 37, mod. yellow orange |
| | DFP | none |
| | AM | none |
| | R | hydrolysis of starch; positive |
| Starch- | G | good |
| Yeast | S | raised, deeply folded |
| Agar | C | g5ni, cocoa brown; 58, moderate brown |
| | DFP | faint yellow |
| | AM | none |
| | R | hydrolysis of starch; positive |
| Casein | G | good |

TABLE II-continued
Growth, Morphology and Reactions on Various Media
*Micromonospora purpurea* strain 1124

| Medium | | Strain |
|---|---|---|
| Agar | S | plicate |
| | C | g5nc, burnt orange; 35 strong red orange |
| | DFP | none |
| | AM | none |
| | R | hydrolysis of casein; positive |
| Tyrosine | G | good |
| Agar | S | plicate |
| (for | C | g5nc, tile red; 55, strong brown |
| hydrolysis) | DFP | none |
| | AM | none |
| | R | hydrolysis of tyrosine; positive |
| Tyrosine | G | poor to fair |
| Agar | S | flat, wrinkled |
| (Melanin | C | g41e, turf tan; 57, light brown |
| Formation | DFP | pinkish red |
| ISP #7) | AM | none |
| | R | melanin formation; negative |
| Peptone | G | fair to good |
| Yeast | S | raised, folded |
| Extract | C | g4pe, orange rust; 51, deep orange |
| Iron Agar | DFP | none |
| (ISP #6) | AM | none |
| | R | hydrogen sulfide formation; negative |
| Dorsett | G | fair |
| Egg Agar | R | liquification of egg; negative |
| Loeffler's | G | good |
| Serum Agar | R | liquification of serum; positive |

G = Growth;
S = Surface;
C = Color;
DFP = Diffusible Pigment;
AM = Aerial Mycelium and
R = Reaction

MICROSCOPIC

The organism exhibits long, branched mycelia, 0.5 microns in diameter. Smooth-walled, spore-like structures are formed terminally; sporophores are not observed.

CHEMICAL

Analysis of whole cells indicates the presence of mesodiaminopimelic acid, xylose and arabinose. The presence of these compounds are indicative of organisms belonging to the genus Micromonospora.

TABLE III
Carbohydrate Utilization and Physiological Characteristics of *M. purpurea* strain 1124

| Test | Reaction | Carbohydrate | Reaction |
|---|---|---|---|
| Hydrolysis of: | | L-Arabinose | good |
| Gelatin | positive | D-Arabinose | fair |
| Starch | positive | Dulcitol | poor |
| Casein | positive | Galactose | poor |
| Tyrosine | positive | Glucose | good |
| Cellulose | positive | Fructose | poor |
| | | Lactose | poor to fair |
| Liquification of: | | Mannitol | poor |
| Egg | negative | Raffinose | poor |
| Serum | positive | Rhamnose | poor |
| | | Ribose | poor to fair |
| Formation of: | | Melizitose | poor |
| Melanin | negative | Glycerol | poor |
| H₂S | negative | Sucrose | good |
| | | Xylose | good |
| Litmus Milk | proteolysis | Salicin | poor |
| | | Monnose | good |
| Nitrate to | | Maltose | good |
| Nitrate | positive | Trehalose | good |
| | | Inulin | poor to fair |
| NaCl Tolerance | 3-4% | | |
| Growth on non-neutralized potato | negative | | |

TABLE III-continued

Carbohydrate Utilization and Physiological Characteristics of *M. purpurea* strain 1124

| Test | Reaction | Carbohydrate | Reaction |
|---|---|---|---|
| Resistance to gentamicin (50 μg/ml) | positive | | |
| Optimum Temperature Range | 28°–37° C. | | |

ANTIBACTERIAL ACTIVITY

The compounds of this invention are broad spectrum antibacterial agent having a substantial in vivo and in vitro antibacterial effect upon gram-positive and gram-negative bacteria. The antibacterial activity of the compounds is determined as follows:

In Vitro

The in vitro antibacterial activity of the compounds of this invention was determined against representative gram-positive and gram-negative bacteria in Mueller-Hinton broth at pH 7.2. The minimal inhibitory concentration (MIC) values in mcg/ml were observed after incubation for 24 hours then for 48 hours.

Based upon the foregoing test procedure, the compounds of this invention exhibit significant activity against strains of Bacilli such as *B. subtilis* 6633; strains of *Straphylococcus aureus*, such as *S. aureus* Wood and *S. aureus* Gray; stains of *Escherichia coli*, such as *E. coli* JR 88, St. Michaels 589, and Baker 2; strains of *Pseudomonas aeruginosa*, such as *P. aeruginosa* NRRL 3223, Stone 39, Stone 20 and St. Michaels 1395. Many of the foregoing bacteria are clinical isolates obtained from subjects having active infections.

In Vivo

The in vivo antibacterial activity of the compounds of this invention may be determined against lethal doses of two species of infectious bacteria in Carworth Farms CF-1 mice weighing about 20 gms. The mice are infected by intraperitoneal infection with a lethal dose ($10^7$ organisms) of either *S. aureus* Gray or *Pseudomonas aeruginosa*. One hour later, the antibacterial agent in the form of the sulfate salt in an aqueous medium is administered sub-cutaneously. Infected, non-treated controls die within 24 hours. The number of survivors are determined 48 hours after infection and the data analyzed by standard probit procedures.

On the basis of the in vitro and in vivo tests, the compounds of this invention may be used to disinfect the surfaces of laboratory equipment, such as tables, scales, cages and the like. They may also be combined with detergents to clean and disinfect laboratory glassware, surgical instruments or the like. Also by virtue of their in vivo activity, the compounds of this invention may be used to treat animals having susceptible bacterial infections. The antibacterial agents of this invention may be admixed with the usual pharmaceutical excipients and compounded into tablets, capsules, syrups and injectable solutions and suspensions.

In view of the fact that the antibacterial agents are elaborated by the methylating microorganisms as complexes of the 3″-N-methyl and the 3″-N-methyl-4″-C-methyl derivatives of the respective antiobiotics, the complexes may be used for the purposes and in the dosage forms described above without being separated from each other. Alternatively, the complexes may be separated during the isolating procedure and may be utilized individually.

In either case, the complexes or the compounds, per se, or their derivatized manifestations (as defined herein) are administered in doses ranging from 2 mg/kg/day to about 25 mg/kg/day in divided doses.

EXAMPLE 1

Preparation of 3″-N-Methyl and 3″-N-methyl-4″-C-methyl tobramycin

A. Inoculum Development

Stage 1

Prepare a medium consisting of the following: beef extract, 3 g; tryptone, 5 g; dextrose, 1 g; potato starch, 24 g; yeast extract, 5 g; calcium carbonate, 2 g; and tap water to 1000 ml.

Divide the medium into 50 ml portions in 250 ml shake flasks and sterilize it.

Inoculate each flask with 2.5 ml of a frozen cell preparation of *M. inyoensis* 1550F-1G or *M. purpurea* SC 1124 and incubate for 48 hours at 28° C. with agitation of about 300 rpm.

Transfer aseptically 2.5 ml of the culture prepared in Stage 1 to 50 ml of fresh broth having the same composition as that used in Stage 1 contained in a 250 ml shake flask. Incubate for an additional 48 hours at 28° C. with agitation at 300 rpm.

B. Fermentation

Prepare a medium consisting of potato dextrin, 50 g; dextrose, 5 g; soybean meal, 35 g; calcium carbonate, 7 g; cobalt chloride, 10-6 mole; and tap water to 1000 ml.

Divide the medum into 50 ml portions in 250 ml shake flasks and sterilize it.

Inoculate each flask with 2.5 ml of the inoculum from Stage 2 and incubate for 1 to 2 days at 28° C. with agitation at 300 rpm. Add tobramycin to a final concentration of 50 to 200 mcg/ml and ferment until the fermentation is complete as determined by periodic sampling. Monitor the methylation by sampling the fermentation mixture at 12 to 24 hour intervals, followed by acidification with sulfuric acid, filtration, neutralization of the filtrate with ammonium hydroxide. Chromatograph the antibiotic complex on a weakly acidic cationic ion exchange resin in the ammonium ($NH_2$) form. Wash the column with deionized water until the washes are color-free, then eulute with dilute (2 N) ammonium hydroxide. Concentrate the eluate to about 25 ml, chromatograph on paper and/or celluelose and bioautograph against *S. aureus* ATCC 6538P.

When the fermentation is complete as determined by bioautograms of the samples *Staphylococcus aureus* ATCC 6538P and by paper or cellulose chromatography, treat the remaining fermentation mixture in the manner described for the samples then lyophilize the concentrated eluate to obtain thereby 3″-N-methyl and 3″-N-methyl-4″-C-methyl tobramycin.

EXAMPLE 2

Preparation of 3″-N-methyl kanamycin A and 3″-N-methyl-4″-C-methyl kanamycin B

A. Inoculum Development

Prepare a viable vegetative inoculum as described in Stages 1 and 2 of Example 1, using either *M. purpurea* SC 1124 or *M. inyoensis* 1550F-1G.

B. Fermentation

Initiate the fermentation as described in Example 1 using kanamycin A at a concentration of 50 to 200 ug/ml of the fermentation broth. Monitor the fermentation as described in Example 1 and when the fermentation is complete, isolate the product as described in Example 1. In this manner, a complex of 3"-N-methyl and 3"-N-methyl-4"-C-methyl kanamycin A is obtained.

EXAMPLE 3

Preparation of 3"-N-methyl kanamycin B and 3"-Methyl-4"-C-methyl kanamycin B

A. Inoculum Development

Prepare a viable vegetative inoculum as described in Stages 1 and 2 of Example 1 using either *M. purpurea* SC 1124 or *M. inyoensis* 1550F-1G.

B. Fermentation

Initiate the fermentation as described in Example 1 using kanamycin B at a concentration of 50 to 200 ug/ml of fermentation broth. Monitor the fermentation as described in Example 1 and when the fermentation is complete, isolate the product as described in Example 1. In this manner, a complex of 3"-N-methyl kanamycin B and 3"-N-methyl-4"-C-methyl kanamycin B is obtained.

EXAMPLE 4

Preparation of 3"-N-methyl kanamycin A and 3"-N-methyl-4"-C-methyl kanamycin A

100 Liter Fermentation

A. Inoculum Medium

| Soy grits | 3.5% |
|---|---|
| Potato dextrin | 5.0% |
| Cerelose | 0.5% |
| Calcium carbonate | 0.5% |
| Cobalt chloride hexahydrate | .002% |
| Soft water q.s. to 10.0 liters | |

Inoculum Development Stage

A. Prepare the inoculum medium set forth above. Transfer 100 ml of the medium to 40 three hundred milliliter shake flasks and sterilize it. Inoculate each flask with 5.0 ml of a partially thawed frozen preparation of *M. inyoensis* 1550F-1G or *M. purpurea* SC 1124 and incubate for 3 days at about 32° C. while agitating the medium at about 300 rpm.

B. To ten 750 ml portions of fresh, sterile inoculum medium in 2.0 liter shake flasks add 38.5 ml of the inoculum prepared in Step A and incubate for 3 days at about 32° C. while agitating the medium at about 200 rpm. Combine the inocula under aseptic conditions.

Fermentation

C. Fermentation Medium

| Potato dextrin | 4.5 kg |
|---|---|
| Soy grits | 3.15 kg |
| Cerelose | .450 kg |
| Calcium carbonate | .450 kg |
| Cobalt chloride | 200 mg |
| Soft water | 90 liters |

D. Fermentation Procedure

Charge the fermentation medium to a 25 gallon fermentor containing 90 liters of soft water. Sterilize the medium for 45 minutes at 121° C. with agitation at from about 175 to about 200 rpm. Cool the medium to about 35° C., adjust the pH to about 7.2°–7.4° C. and introduce air into the medium at a rate of about 1.5 to 2.0 cubic feet per minute (cfm). Add 5.25 liters of the inoculum prepared in Step B. Allow the microorgaism to grow for about 48 hours, then add 17.5 g of kanamycin sulfate dissolved in 3.0 liters of sterile water. Allow the fermentation to proceed for 24 hours then commence taking samples. Treat the samples as described in Example 1, and when the fermentation is complete, treat as described in Step E below.

E. Isolation of Products

Charge the fermentation mixture to a glass lined vessel and add 600 gms of oxalic acid (pH 3.5–3.9). Adjust to pH 2.0 with 12 N sulfuric acid (600–625 mls) and filter. Adjust the filtrate to pH 7.0 using dilute ammonium hydroxide. Feed the solution to a 2 inch chromatographic column containing 1 liter of IRC-50 resin in the $NH^+4$ form at a flow rate of about 120–150 mls/min. Wash the column with 4.0 liters of deionized water downflow then with 10.0 liters upflow. Elute the column with about 3.0 lters dilute ammonium hydroxide at about 80 mls/min. while collecting 250 ml fractions. Sample each fraction for bioautography against *S. aureus* ATCC 6538P. Combine the fractions having the major portion of active material. Concentrate the combined fractions and lyophilize to obtain thereby a complex containing 3"-N-methyl kanamycin A and 3"-N-methyl-4"-C-methyl kanamycin A. Separation of the complex into the individual components may be effected by chromatography on silica gel using, as the developing solvent, the lower phase of a chloroform-:methanol:ammonium hydroxide (1:1:1) v/v solvent system.

Similarly, subjecting dibekacin to the processes of the foregoing example yields 3"-N-methyl-4"-C-methyl dibekacin 3"-N-methyl dibekacin.

The foregoing examples are effective for the preparation of all of the compounds of this invention. Chromatography on a suitable absorbent such as silica gel is suitable for the resolution of the antibiotic complexes into the individual components of which they are composed.

The derivatization of the methylated analogs produced by the process of this invention, e.g., the formation of the 5-epi, 5-deoxy, 5-epiamino-5-deoxy, 5-epiazido-5-deoxy and the 5-epifluoro-5-deoxy analogs of 3"-N-methyl tobramycin, 3"-N-methyl-4"-C-methyl tobramycin, 3"-N-methyl kanamycin a, 3"-N-methyl-4"-C-methyl kanamycin A, 3"-N-methyl kanamycin B, 3"-N-methyl-4"-C-methyl kanamyci B, 3"-N-methyl dibekacin and 3"-N-methyl-4"-C-methyl dibekacin and the formation of the 1-N-X analogs (as herein defined) of all the foregoing, and conversion of such compounds to their pharmaceutically acceptable acid addition salts may be all done according to methods known to those of ordinary skill in the art.

Indeed, the 5-epi analogs may be prepared by the methodology described in U.S. Pat. No. 4,000,261; the 5-deoxy analogs may be prepared by the methods described in U.S. Pat. No. 4,053,591; the 5-epiamino-5-deoxy analogs and the 5-epiazido-5-deoxy analogs may be prepared by the methods described in U.S. Pat. No. 4,000,262. The 5-epifluoro-5-deoxy analogs may be prepared by the methods described in South Africa Patent No. 0385, issued on Dec. 6, 1978 on an application filed on Jan. 20, 1978. The 1-N-X analogs (as herein defined) of the foregoing may be prepared by methods described in the art, particularly that set forth in U.S. Pat. Nos. 4,117,221 and 4,029,882, as well as the methods described by T. L. Nagabhushan, et al in The Journal of of the American Chemical Society, Vol. 100, page 5253 (1973) entitled "Interaction of Vicinal and Non-Vicinal Amino-Hydroxy Group Pairs in Aminoglycoside-Aminocyclitol Antibiotics with Transition Metal Cations Selective-N-Protection" which describes the methods for preparing the necessary intermediates useful in preparing the 1-N-X derivatives.

The 1-N-X analogs, as herein defined, may be prepared in the S or the R configuration or in the form of a racemic mixture thereof. All aspects are contemplated as being within the scope of this application.

The non-toxic acid addition salts of the products of the invention may be prepared by methods known in the art. Among the acids whose salts are contemplated are the inorganic and organic acids generally associated with analogous aminoglycosine antibiotics, particularly those derived from hydrochloric, sulfuric and phosphoric acids.

We claim:

1. A compound selected from the group consisting of (a) the 3''-N-methyl-4''-C-methyl analogs of tobramycin, kanamycin A, kanamycin B, and dibekacin, (b) the 5-epi, the 5-deoxy, 5-epiamino-5-deoxy, 5-epizido-5-deoxy and 5-epifluoro-5-deoxy analogs of 3''-N-methyl tobramycin, 3''-N-methyl-4''-C-methyl tobramycin, 3''-N-methyl kanamycin A, 3''-N-methyl-4''-C-methyl kanamycin B, 3''-N-methyl dibekacin, 3''-N-methyl-4''-C-methyl dibekacin and (c) the 1-N-X analogs of compounds of (a) and (b), wherein X is a ($C_1$–$C_8$) alkyl or a ($C_1$–$C_8$) acyl group which may bear substituents selected from the group consisting of amino, ($C_1$–$C_8$) lower alkylamino and hydroxy, with the proviso that not more than one substituent can be on the same carbon atom—and to the pharmaceutically acceptable non-toxic acid addition salts thereof.

2. A compound of claim 1 wherein said compound is selected from the group designated (a), and the non-toxic pharmaceutically acceptable salts thereof.

3. A compound of claim 1 wherein said compound is selected from the group consisting of (b), and the non-toxic pharmaceutically acceptable acid addition salts thereof.

4. A compound of claim 1 wherein said compound is selected from the group consisting of (c), and the non-toxic pharmaceutically acceptable acid addition salts thereof.

5. 1-N-[S-3-amino-2-hydroxypropionyl]-4''-C-methyl-3''-N-methyl-5-epikanamycin A.

6. 4''-C-methyl-3''-N-methyl-5-epikanamycin A.

7. 4''-C-methyl-3''-N-methyl tobramycin.

8. 4''-C-methyl-3''-N-methyl kanamycin A.

* * * * *